United States Patent [19]

Maass et al.

[11] 4,079,070

[45] Mar. 14, 1978

[54] PREPARATION OF CYCLIC DIPHENYLSILOXANES

[75] Inventors: Günther Maass, Cologne; Hans-Joachim Lücking, Opladen; Joachim Maas, Leverkusen; Klaus Seyfried, Schildgen, all of Germany

[73] Assignee: Bayer Aktiengesellschaft, Leverkusen, Germany

[21] Appl. No.: 709,993

[22] Filed: Jul. 30, 1976

[30] Foreign Application Priority Data

Aug. 13, 1975 Germany ............................ 2536010

[51] Int. Cl.² .................................... C07F 7/08
[52] U.S. Cl. ................................ 260/448.2 E
[58] Field of Search ................... 260/448.2 E

[56] References Cited

U.S. PATENT DOCUMENTS

| 3,484,469 | 12/1969 | Guinet et al. | 260/448.2 E |
| 3,607,898 | 9/1971 | Macher | 260/448.2 E |
| 3,983,148 | 9/1976 | Reedy et al. | 260/448.2 E |

OTHER PUBLICATIONS

Noll, "Chemistry and Technology of Silicones", Academic Press, N.Y. (1968), pp. 192–196.

*Primary Examiner*—Paul F. Shaver
*Attorney, Agent, or Firm*—Burgess, Dinklage & Sprung

[57] ABSTRACT

In the preparation of a cyclic diphenylsiloxane of the formula

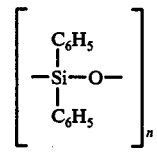

wherein $n$ is 3 or 4, by hydrolysis of a diphenyldihalogenosilane, the improvement which comprises adding the diphenyldihalogenosilane, in the presence of an organic, aprotic solvent to an aqueous basic solution, the base being employed in an amount which is at least stoichiometrically equivalent to the halogen content, whereby the cyclic diphenylsiloxane is obtained in high yield and purity. The base is preferably lithium hydroxide, potassium hydroxide or sodium hydroxide and is used in the form of an at least 5 molar solution, about 2.1 to 2.5 equivalents being used per mole of diphenyldihalogenosilane.

5 Claims, No Drawings

PREPARATION OF CYCLIC DIPHENYLSILOXANES

The present invention relates to a process for the preparation of cyclic diphenylsiloxanes of the formula

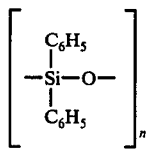

wherein n is 3 or 4.

It is known that the spectrum of properties of pure methylpolysiloxanes is favorably influenced in many respects by the incorporation of diphenylsiloxy groups. Thus, the resistance to radiation and the heat stability as well as the non-flammability increase sharply and, if the compound is a silicone rubber, it is also possible for the low-temperature flexibility, the mechanical properties when hot and the transparency to be decisively improved. The use of methylphenylpolysiloxanes of this type is, however, associated with sharply increased costs, which result from the preparation of the material which supplies diphenylsiloxy groups, that is octaphenylcyclotetrasiloxane and hexaphenylcyclotrisiloxane. These two compounds can be obtained as crystalline substances in a very pure form and then guarantee that no monofunctional or trifunctional units, which would impair the properites of the siloxane, are carried over during the copolymerization with octamethylcyclotetrasiloxane.

Hexaphenylcyclotrisiloxane and octaphenylcyclotetrasiloxane can be prepared from various starting materials. A known reaction is the condensation of diphenylsilanediol in the presence of various catalysts. Catalysts which can be used are, for example, strong acids, such as sulfuric acid, acetic anhydride, amines or alkali metal hydroxides (compare, for example, J. Chem. Soc. 101, 2125 (1912), Chem. Ber. 38, 4132 (1905), Nippon Kagaku Zasshi 84, 422 (1963) and British Patent Specification No. 947,249). The diphenylsilanediol required is prepared according to known methods by hydrolysis of diphenyldichlorosilane. The disadvantage of this two-stage process is that the cyclic siloxanes are formed to the extent of only about 60%; in addition, a large proportion of undesired condensation products, the separation of which from the cyclic compounds is also associated with difficulties, is also formed.

Considerable efforts have already been undertaken to find an economic process, which is simple to use, for the preparation of cyclic diphenylsiloxanes of this type. In J. Org. Chem. 24, 861 (1959), a process is described in which diphenyldichlorosilane is reacted in acetone with ammonium thiocyanate. This process gives mainly hexaphenylcyclotrisiloxane, but the product is highly contaminated with polythiocyanic acids.

Hexaphenylcyclotrisiloxane and octaphenylcyclotetrasiloxane can also be prepared by reacting diphenyldichlorosilane with dimethylsulfoxide (compare, for example, French Patent Specification 1,456,981).

The mixture formed in this case has an unpleasant odor and contains highly acid sulfur-containing substances, from which it can be freed only by involved purification steps. According to another known method (I. Org. Chem. 25, 310 (1960)), hexaphenylcyclotrisiloxane is preferably formed from diphenyldichlorosilane in organic solvents using zinc oxide. However, because of the high cost of zinc oxide and because of the yields (65% of hexaphenylcyclotrisiloxane), this process is also uneconomic for industrial use. U.S. Patent Specification No. 3,110,720 describes the reaction of diphenyldichlorosilane with alkali metal oxides or alkali metal carbonates or alkaline earth metal carbonates at 200° – 450° C to give octaphenylcyclotetrasiloxane. Despite these high temperatures, which can lead to side reactions, the reaction proceeds only incompletely and, when working up, the unreacted diphenyldichlorosilane and the chlorine-containing linear diphenylsiloxanes must be separated off under anhydrous conditions. Because of the moderate yields and the high expenditure during working up, this process also has serious disadvantages.

In addition to the two starting materials described, that is diphenylsilanediol and diphenyldichlorosilane, dichlorooctaphenyltetrasiloxane, which according to German Published Specification DOS 2,036,616 can be converted into octaphenylcyclotetrasiloxane by means of alkali metal carbonates, also has a certain importance. However, this starting compound is difficult to prepare in the necessary purity and the process also has the disadvantage of being two-stage.

The subject of the present invention is therefore a process for the preparation of cyclic diphenylsiloxanes of the general formula

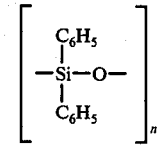

wherein n represents 3 or 4, by hydrolysis of diphenyldihalogenosilanes, which is characterized in that a diphenyldihalogenosilane, in the presence of organic, aprotic solvents, is added to an aqueous basic solution, the base being employed in an amount which is at least stoichiometrically equivalent to the halogen content of the halogenosilane.

Surprisingly, it has been found that octaphenylcyclotetrasiloxane and hexaphenylcyclotrisiloxane, which are free from higher-molecular products, are obtained in almost quantitative yield when a diphenylhalogenosilane, for example diphenyldichlorosilane or diphenyldibromosilane, in the presence of an organic aprotic solvent, is added dropwise to a basic aqueous solution, for which reaction the weight ratio of solvent to water must be at least 0.2 : 1 and about 2.0 to about 2.5 equivalents of the base must be employed per mole of diphenyldihalogenosilane.

This mode of reaction is particularly astonishing especially because it would have been expected according to the state of the art that an excess of alkali metal hydroxide solution would lead to the formation of siloxanes of high molecular weight, as is known from other investigations (compare, for example, W. Noll, Chemie und Technologie der Silicone (Chemistry and Technology of Silicones) (1968), page 167; and J. Amer. Chem. Soc. 68, 358 (1949)). Splitting of the silicon-phenyl bonds, which was to be expected, is also not observed.

Suitable bases are, in particular, the alkali metal hydroxides, such as, for example, KOH, NaOH or LiOH, but, in principle, the reaction can also be carried out with alkali metal carbonates, alkaline earth metal hydroxides, ammonia or amines. The amount of base should preferably be between about 2.1 and 2.5 equivalents per mole of diphenyldihalogenosilane.

Organic solvents which can be used are, in particular, ketones, preferably acetone, and water-soluble ethers. Mixtures of these solvents with toluene or xylene can also be employed. On the other hand, alcohols and solvents which react with alkali are less suitable. The solvent — at least 20% by weight of the water employed — either can be initially introduced with the aqueous base or is admixed with the diphenyldihalogenosilane.

During the reaction, the temperatures are appropriately kept above about 40° C, preferably between about 60° and 100° C. The process according to the invention can be carried out by initially introducing the aqueous basic solution at about 60° C and adding the mixture of solvent and diphenyldihalogenosilane dropwise at such a rate that the solvent boils gently under reflux. When the addition is complete, the solvent is distilled off under normal pressure and the crystalline cyclic diphenylsiloxanes are washed and separated off from the basic salt solution according to known methods. The amount of water employed for the preparation should be so large that the basic halide formed does not precipitate out after the solvent is removed. For special purposes the product can, for example, be recrystallized from toluene.

According to a particular embodiment of the process according to the invention, the mixture of solvent and diphenyldihalogenosilane is added dropwise to the necessary amount of alkali metal hydroxide, which is present as an at least 5 molar solution. Under such reaction conditions, pure octaphenylcyclotetrasiloxane is formed, after the working-up steps described above, in its metastable crystal modification (melting point 187° C).

The advantage of the process according to the invention which has been described is that low molecular cyclic diphenylsiloxanes are formed almost quantitatively in one step from diphenylhalogenosilanes, especially from relatively cheap diphenyldichlorosilane, when a base is employed.

The resulting mixture of hexaphenylcyclotrisiloxane and octaphenylcyclotetrasiloxane, as well as the octaphenylcyclotetrasiloxane prepared according to the special embodiment, can be synthesised with octamethylcyclotetrasiloxane by copolymerization in the presence of KOH to give a methylphenylpolysiloxane. If, for example, about 10% by weight of octaphenylcyclotetrasiloxane are copolymerized with 90% by weight of octamethylcyclotetrasiloxane and this mixture is further processed to give a silicone rubber, a product is obtained which has rubber properties which disappear only at −90° C. For the diphenylsiloxy-free mixture, the corresponding temperature is already reached at −45° C.

The Examples which follow are intended to illustrate the process according to the invention in even more detail.

EXAMPLE 1

1 kg of NaOH in 4 l of water was initially introduced into a flask and heated to 60° C. 2 kg of diphenyldichlorosilane in 2 l of acetone were then added dropwise, while stirring vigorously, at such a rapid rate that the acetone boiled moderately under reflux without heating. When the addition was complete, the acetone was distilled off until a top temperature of 100° C was reached. After adding 3 l of water to the residue, the suspension was cooled to room temperature. The octaphenylcyclotetrasiloxane which had precipitated was filtered off and washed with water until free from chloride and alkali. After drying at 120° C, the product had a melting point of 187° C. Yield: 1,490 g (95%).

EXAMPLE 2

The quantities and process steps were as in Example 1 except that the acetone was initially introduced with the sodium hydroxide solution and the chlorosilane was added dropwise in the undiluted state. The yield of octaphenylcyclotetrasiloxane with a melting point of 186° C was 96%.

EXAMPLE 3

A mixture of 510 g of diphenyldichlorosilane in 500 ml of acetone was added dropwise in the course of 3 hours to a hot solution, at 60° C, of 340 g of KOH in 1 l of water, while stirring vigorously. The acetone and a little water were then distilled off and, after cooling the residue, the crystalline octaphenylcyclotetrasiloxane was filtered off and washed with water. After drying, 376 g (94% yield) of octaphenylcyclotetrasiloxane of melting point 187° C (metastable crystal modification) were obtained. After recrystallization from toluene, the product had a melting point of 201° C.

EXAMPLE 4

The process of Example 1 was repeated but 2 l of 1,4-dioxane were used in place of 2 l of acetone. Octaphenylcyclotetrasiloxane of melting point 185° C was formed in 96% yield.

COMPARISON EXAMPLE: (not according to the invention)

The process steps and quantities were as selected in Example 3 except that an equal amount of methanol was used in place of the acetone. The resulting non-homogeneous product was greasy and had a melting range of 270° − 290° C.

It will be appreciated that the instant specification and examples are set forth by way of illustration and not limitation, and that various modifications and changes may be made without departing from the spirit and scope of the present invention.

What is claimed is:

1. In the preparation of a cyclic diphenylsiloxane of the formula

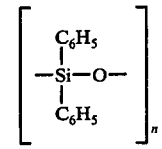

wherein $n$ is 3 or 4, by hydrolysis of a diphenyldihalogenosilane, the improvement which comprises adding the diphenyldihalogenosilane, in the presence of an organic, aprotic solvent to an aqueous basic solution, the base being employed in an amount which is at least stoichiometrically equivalent to the halogen content, whereby the cyclic diphenylsiloxane is obtained in high yield and purity.

2. The process according to claim 1, wherein the base of the basic solution is at least one of lithium hydroxide, potassium hydroxide and sodium hydroxide.

3. The process according to claim 1, wherein the base is used in the form of an at least 5 molar solution.

4. The process according to claim 1, wherein the weight ratio of solvent to water is at least 0.2:1.

5. The process according to claim 4, wherein the base is used in the form of an at least 5 molar solution and the amount of the base is from about 2.1 to 2.5 equivalents per mole of diphenyldihalogenosilane, the base being at least one of lithium hydroxide, potassium hydroxide and sodium hydroxide.

* * * * *